United States Patent
Chen et al.

(10) Patent No.: US 11,130,732 B2
(45) Date of Patent: Sep. 28, 2021

(54) METHOD AND DEVICE FOR PREPARING 2-HYDROXY-4-METHYLTHIOBUTYRIC ACID AND INTERMEDIATES THEREOF

(71) Applicants: ZHEJIANG NHU COMPANY LTD., Shaoxing (CN); ZHEJIANG UNIVERSITY, Hangzhou (CN); SHANDONG NHU AMINO ACID CO., LTD., Weifang (CN)

(72) Inventors: Zhirong Chen, Zhejiang (CN); Hong Yin, Zhejiang (CN); Baishan Hu, Shaoxing (CN); Zhengjiang Wang, Weifang (CN); Zhixuan Wang, Weifang (CN); Cong Chen, Weifang (CN); Guisheng Qiu, Shaoxing (CN); Qichuan Li, Shaoxing (CN); Qingai Shi, Shaoxing (CN)

(73) Assignees: ZHEJIANG NHU CO., LTD., Shaoxing (CN); ZHEJIANG UNIVERSITY, Hangzhou (CN); SHANDONG NHU AMINO ACID CO., LTD., Weifang (CN)

( * ) Notice: Subject to any disclaimer, the term of this patent is extended or adjusted under 35 U.S.C. 154(b) by 0 days.

(21) Appl. No.: 17/263,362

(22) PCT Filed: Aug. 27, 2019

(86) PCT No.: PCT/CN2019/102680
§ 371 (c)(1),
(2) Date: Jan. 26, 2021

(87) PCT Pub. No.: WO2020/088060
PCT Pub. Date: May 7, 2020

(65) Prior Publication Data
US 2021/0147350 A1    May 20, 2021

(30) Foreign Application Priority Data
Nov. 1, 2018  (CN) .................. 201811296139.X

(51) Int. Cl.
*C07C 319/20*  (2006.01)
*C07C 319/18*  (2006.01)
*B01J 19/24*   (2006.01)
*C07C 319/28*  (2006.01)
*C07C 323/52*  (2006.01)

(52) U.S. Cl.
CPC .............. *C07C 319/20* (2013.01); *B01J 19/24* (2013.01); *C07C 319/18* (2013.01); *C07C 319/28* (2013.01); *C07C 323/52* (2013.01)

(58) Field of Classification Search
CPC .................................................. C07C 319/20
See application file for complete search history.

(56) References Cited

U.S. PATENT DOCUMENTS

| 2,745,745 | A | | 5/1956 | Blake |
| 4,225,516 | A | * | 9/1980 | Biola .................... C07C 323/00 568/41 |
| 4,912,257 | A | | 3/1990 | Hernandez et al. |
| 4,960,932 | A | | 10/1990 | Gillonnier et al. |
| 5,352,837 | A | * | 10/1994 | Hsu ........................ C07C 45/35 568/41 |
| 5,663,409 | A | * | 9/1997 | Blackburn ............ C07C 319/18 558/351 |
| 5,856,567 | A | * | 1/1999 | Hsu ....................... C07C 319/20 562/581 |
| 2014/0051890 | A1 | | 2/2014 | Finkeldei et al. |

FOREIGN PATENT DOCUMENTS

| CN | 1148041 A | 4/1997 |
| CN | 1277816 C | 10/2006 |
| CN | 101812004 A | 8/2010 |
| CN | 102796030 A | 11/2012 |
| CN | 103347854 A | 10/2013 |

(Continued)

OTHER PUBLICATIONS

English translation of Written Opinion of the ISA for PCT/CN2019/102680 (3 pages).
English translation of International Search Report for PCT/CN2019/102680 (3 pages).
PCT Publication WO 2020/088060 A1 for PCT/CN2019/102680 with English translation (62 pages).
PCT Publication WO 2020/088060 A1 for PCT/CN2019/102680.

*Primary Examiner* — Rosalynd A Keys
(74) *Attorney, Agent, or Firm* — Young Basile Hanlon & MacFarlane, P.C.

(57) ABSTRACT

Provided by the present disclosure are a method and a device for preparing 2-hydroxy-4-methylthiobutyric acid and intermediates thereof; the intermediates for preparing 2-hydroxy-4-methylthiobutyric acid comprise 3-methylthiopropionaldehyde and 2-hydroxy-4-methylthiobutyronitrile. The method for preparing 2-hydroxy-4-methylthiobutyric acid provided by the present disclosure comprises: step (1), a step of reacting acrolein with methyl mercaptan to prepare 3-methylthiopropionaldehyde; step (2), a step of reacting 3-methylthiopropionaldehyde with hydrocyanic acid to prepare 2-hydroxy-4-methylthiobutyronitrile; and step (3), a step of hydrating 2-hydroxy-4-methylthiobutyronitrile by using sulfuric acid and then hydrolyzing to prepare 2-hydroxy-4-methylthiobutyric acid; wherein in steps (1), (2) and (3), the reaction status of the materials is detected online, and the proportions of the materials are controlled according to the detection results such that reactions are performed completely.

16 Claims, 3 Drawing Sheets

(56) References Cited

FOREIGN PATENT DOCUMENTS

| CN | 103476747 A | 12/2013 | | |
|---|---|---|---|---|
| CN | 104262216 A | 1/2015 | | |
| CN | 104428285 A | 3/2015 | | |
| CN | 105732450 A | 7/2016 | | |
| CN | 107628976 A | 1/2018 | | |
| GN | 101735124 A | 6/2010 | | |
| WO | WO-0110776 A1 * | 2/2001 | ………… | C07C 319/04 |

* cited by examiner

METHOD AND DEVICE FOR PREPARING 2-HYDROXY-4-METHYLTHIOBUTYRIC ACID AND INTERMEDIATES THEREOF

CROSS-REFERENCE TO RELATED APPLICATIONS

This application is a 371 National Stage Entry of the International Application No. PCT/2019/102680, published as WO2020/088060, filed on 27 Aug. 2019, which claims priority to Chinese Application No. 201811296139.X filed on 1 Nov. 2018, both of which are incorporated by reference here in their entirety.

TECHNICAL FIELD

The present disclosure relates to a method and a device for preparing chemical products, and specifically relates to a method and a device for preparing 2-hydroxy-4-methylthiobutyric acid and intermediates thereof.

BACKGROUND

2-Hydroxy-4-methylthiobutyric acid, also referred to as liquid methionine or methionine hydroxy analogue, is used as a feed additive and may also be used as a methionine nutritional supplement, so as to promote the growth and development of animals. According to the literature reports, liquid methionine has a biological potency that is not much different from that of methionine and the synthetic process is relatively simple, thereby having good market prospect.

Currently, the method for producing 2-hydroxy-4-methylthiobutyric acid in industrial field mainly adopts acrolein (simply referred to as ACR) as a raw material. Acrolein is first reacted with methyl mercaptan under the action of the catalyst to prepare and obtain 3-methylthiopropionaldehyde (simply referred to as MMP), then gaseous or liquid hydrocyanic acid and 3-methylthiopropionaldehyde are used to prepare 2-hydroxy-4-methylthiobutyronitrile (simply referred to as cyanohydrin) under the action of the catalyst, and 2-hydroxy-4-methylthiobutyronitrile is hydrolyzed in the presence of sulfuric acid to obtain 2-hydroxy-4-methylthiobutyric acid, that is, liquid methionine.

The materials involved in the above-mentioned reaction process are either malodorous (for example, $CH_3SH$) or highly toxic (for example, HCN and $CH_2=CHCHO$). Therefore, there are quite high requirements for the safety of operation during the production process. If the preparation process is not monitored timely, considerable safety risks may be caused. In addition, the excessive addition of the above-mentioned raw materials (i.e., acrolein and hydrocyanic acid) may cause some undesirable side reactions. For example, excess acrolein and MMP may form polymers, which results in the formation of a high-boiling residue; while excess HCN (as described in CN1277816C, U.S. Pat. Nos. 4,960,932 and 4,912,257) not only reduces the safety of operation but also generates formic acid during the process of hydrolysis reaction, ammonium formate is formed after neutralization, thus reducing the quality of ammonium sulfate recovered in the later period.

In the patent published as CN101812004A, Degussa has proposed a method for preparing 3-methylthiopropionaldehyde and 2-hydroxy-4-methylthiobutyronitrile. The reaction is carried out continuously in a fixed reaction bed. In order to maintain a favorable conversion rate and low degradation of the reactants, a slightly excessive amount of methyl mercaptan needs to be maintained in the reaction mixture, and the range of excess is controlled between 0.05% and 0.2%. If crude MMP is used for the next reaction, the reaction is also carried out in an excessive amount of hydrocyanic acid, the range of excess is controlled between 0.05% and 1%, the feeding amount of hydrocyanic acid is controlled by using a hydrocyanic acid metering device during the reaction process, and the purity of the finally obtained cyanohydrin is about 92%. It is mentioned in this patent that acrolein and methyl mercaptan are reacted in substantially equivalent amounts in terms of stoichiometric amount, however, the control method for achieving the purpose is not described. Hydrocyanic acid is metered by using a metering device, due to the existence of the side reaction (that is, the polymerization of hydrocyanic acid), the metering alone is actually unable to ensure that the stoichiometric ratio of the raw materials in the system meets the designed requirement. As could be seen from the examples, cyanohydrin obtained by this method has a low purity and may not be directly used for the preparation of 2-hydroxy-4-methylthiobutyric acid.

In the patent published as CN1510030A, Novus has proposed a method for preparing 3-methylthiopropionaldehyde and 2-hydroxy-4-methylthiobutyronitrile, wherein methyl mercaptan is added into a liquid reaction medium in an amount that is at least substantially equivalent to the stoichiometric amount of acrolein on a molar basis. A slightly excessive amount of methyl mercaptan may be employed, and the molar ratio of methyl mercaptan to acrolein is about 1 to 1.02. 3-Methylthiopropionaldehyde obtained by the reaction may be directly reacted with hydrocyanic acid and used to prepare 2-hydroxy-4-methylthiobutyronitrile without the need of removing high-boiling impurities or low-boiling impurities in advance. Hydrocyanic acid is slightly excessive by 2% with respect to 3-methylthiopropionaldehyde. The prepared 2-hydroxy-4-methylthiobutyronitrile is directly used for the preparation of liquid methionine. 2-Hydroxy-4-methylthiobutyric acid obtained via extractive steam distillation is an 85% to 90% aqueous solution. All the intermediates in this patent are used directly. Among these, however, the content of 3-methylthiopropionaldehyde is 89.9% and impurities such as acrolein and methyl mercaptan exist. Nevertheless, as for cyanation reaction, the examples show that the distilled 3-methylthiopropionaldehyde is used and a resultant containing 98.2% 2-hydroxy-4-methylthiobutyronitrile and 0.03% 3-methylthiopropionaldehyde is obtained. It could be seen that, if 3-methylthiopropionaldehyde and 2-hydroxy-4-methylthiobutyronitrile are directly used in the next reaction without being subjected to any treatment, 2-hydroxy-4-methylthiobutyric acid with low purity is obtained.

It is proposed in the patent published as CN101735124A that, when impurities such as mercaptan are contained in methylthiopropionaldehyde, these impurities or derivatives may corrode the reaction vessels and pipes during the hydrolysis process, therefore, there is a need to control the amount of methyl mercaptan. Distillation is employed in this patent to purify 3-methylthiopropionaldehyde. If 2-hydroxy-4-methylthiobutyronitrile does not meet the requirements of the reaction, said substance is further required to be subjected to post-treatment or purified by distillation before being introduced into the next step.

In the patent published as U.S. Pat. No. 2,745,745, Monsanto has disclosed a method for preparing 2-hydroxy-4-methylthiobutyric acid, wherein cyanohydrin is obtained by reacting MMP and HCN in a medium containing pyridine or amine, HCN is also in an excessive amount during the reaction process, and the excess HCN needs to be removed after the reaction is completed. In this patent, a method of conducting distillation under certain pressure is selected to remove the excess HCN.

In the patent published as CN1148041, disclosed is a method for preparing cyanohydrin by reacting gaseous hydrocyanic acid with MMP. A reactive absorption column with plates is employed in this method, that is, a gas flow containing hydrocyanic acid is introduced from the bottom of the reactive absorption column with plates, while aqueous MMP solution containing a buffer solution is introduced from the top of the column. In order to increase the reaction rate, an excessive amount of HCN is also added in MMP. In order to recover the remaining unreacted HCN and MMP contained in the waste gas of the reactive absorption column, an additional washing column is installed at the top of the reactive absorption column, water is used to wash said unreacted HCN and MMP, the water for washing is introduced to the product, thereby resulting in that the water content in the product reaches about 48%. Accordingly, the reaction product needs to be further subjected to post-treatment operations such as distillation, otherwise it could not be used in the next hydrolysis reaction. As for the large-scale production of methionine, the above-mentioned distillation method consumes much energy and is undesirable. In addition, the reaction of preparing cyanohydrin by using hydrocyanic acid and methylthiopropionaldehyde is a reversible exothermic reaction and decomposition may occur during the distillation process, thereby reducing the yield of the final product.

In the patent published as U.S. Pat. No. 4,225,516, the preparation of MMP is carried out in a stirred tank reactor equipped with an external circulation cooling system. If the reaction is not complete within the prescribed residence time, the mixture is then supplied to the second reactor (for example, a plug flow reactor) to enable a complete reaction. It could be seen that prolonging the residence time of MMP reaction may also increase the conversion rates of acrolein and methyl mercaptan and reduce the residual of acrolein and methyl mercaptan.

In the patent published as CN103347854, Degussa has disclosed a method for preparing cyanohydrin. In this method, 3-methylthiopropionaldehyde is reacted with hydrocyanic acid in the presence of an alkali catalyst in the main reaction zone to form cyanohydrin, and HCN is used in an amount of 1.05 mol with respect to 1 mol of 3-methylthiopropionaldehyde. The main reaction zone is a stirred reactor or a loop reactor. The residual gaseous hydrocyanic acid leaving the main reaction zone after the completion of the reaction is absorbed and then further reacted with the materials in the post-reaction zone. The MMP material usually contains a small amount of methyl mercaptan, the excess methyl mercaptan is reacted with acrolein in the post-reaction zone to form MMP, followed by a reaction with HCN to form cyanohydrin at the same time. Finally, a cyanohydrin product with a content of 86% to 97% is obtained, and the content of cyanohydrin fluctuates greatly.

In summary, the raw materials and intermediates involved in the preparation process of liquid methionine are either malodorous or highly toxic, which makes it difficult for direct sampling and analysis. However, if the yield of each step is expected to be improved during the preparation process, the proportions of the raw materials in each step need to be adjusted precisely, but no solution has been provided by the prior art.

SUMMARY

Problems to be Solved by the Disclosure

Regarding the above-mentioned problems, the present disclosure provides a method for continuously preparing 2-hydroxy-4-methylthiobutyric acid, wherein acrolein is used as the starting material and is first reacted with methyl mercaptan to obtain 3-methylthiopropionaldehyde, 3-methylthiopropionaldehyde is reacted with hydrocyanic acid to obtain 2-hydroxy-4-methylthiobutyronitrile, and 2-hydroxy-4-methylthiobutyronitrile is hydrated by using sulfuric acid and then hydrolyzed to obtain 2-hydroxy-4-methylthiobutyric acid. In the present disclosure, the reaction status of the materials is detected by setting online detection devices in each stage of the reaction, and the proportions of the materials are controlled according to detection results, so as to enable a complete reaction.

Means for Solving the Problems

The first aspect of the present disclosure is to provide a method for preparing 3-methylthiopropionaldehyde as an intermediate of 2-hydroxy-4-methylthiobutyric acid, wherein the method comprises: reacting acrolein with an excessive amount of methyl mercaptan in the presence of a catalyst to obtain a pre-reaction solution of 3-methylthiopropionaldehyde; conducting an online detection of a content of hemiacetal in the pre-reaction solution of 3-methylthiopropionaldehyde, and determining a supplementary amount of acrolein according to detection results; and mixing and reacting the supplemented acrolein with the pre-reaction solution of 3-methylthiopropionaldehyde to enable a complete reaction of the hemiacetal contained in the pre-reaction solution of 3-methylthiopropionaldehyde, so as to prepare and obtain 3-methylthiopropionaldehyde.

Further, the feeding molar ratio of acrolein to methyl mercaptan is 0.95:1 to 0.99:1, preferably 0.97:1 to 0.98:1.

Further, the catalyst is selected from organic bases, inorganic bases, or salts formed by tertiary amines and acids, and is preferably a salt formed by a tertiary amine and 2-hydroxy-4-methylthiobutyric acid; the tertiary amine is one or more of triethylamine, tri-n-propylamine, tri-n-butylamine, triisopropylamine, and N,N-dimethylbenzylamine; and the molar ratio of the tertiary amine to 2-hydroxy-4-methylthiobutyric acid is 1.05:1 to 2.0:1, preferably 1.1:1 to 1.5:1.

Further, the addition amount of the catalyst is 0.05% to 0.5% and preferably 0.1% to 0.3% of the total mass of the added acrolein and methyl mercaptan.

Further, the reaction between acrolein and the excessive amount of methyl mercaptan and the reaction between the supplemented acrolein and the pre-reaction solution of 3-methylthiopropionaldehyde have a reaction temperature of 20 to 60° C., preferably 20 to 40° C.

Further, the method for preparing 3-methylthiopropionaldehyde as an intermediate of 2-hydroxy-4-methylthiobutyric acid further comprises a step of conducting an online detection of the residual amount of hemiacetal in the obtained 3-methylthiopropionaldehyde and adjusting the supplementary amount of acrolein according to detection results.

Further, an online Raman spectroscopic detection method is employed in the online detection.

Further, the reaction between acrolein and the excessive amount of methyl mercaptan is carried out in a first reactor R1, and the reaction between the supplemented acrolein and the pre-reaction solution of 3-methylthiopropionaldehyde is carried out in a second reactor R2.

Further, the first reactor R1 is a recirculation reactor, and the second reactor R2 is a plug flow reactor.

Further, the first reactor R1 is a tower reactor or a multi-stage stirred reactor, preferably a tower reactor with baffle plate(s) arranged inside.

Further, an online Raman spectroscopic detector D1 is provided at an outlet of the first reactor for online detection of the content of hemiacetal in the pre-reaction solution of 3-methylthiopropionaldehyde.

Further, an online Raman spectroscopic detector D2 is provided at an outlet of the second reactor for online detection of the content of hemiacetal in 3-methylthiopropionaldehyde.

Further, a part of the pre-reaction solution of 3-methylthiopropionaldehyde enters the second reactor R2, the rest part is used as circulating materials of the first reactor R1, and the ratio of the amount of materials entering the second reactor R2 to the amount of materials used as the circulating materials of the first reactor R1 is 1:10 to 1:50, preferably 1:15 to 1:30.

Further, 3-methylthiopropionaldehyde obtained by preparation is used for preparing 2-hydroxy-4-methylthiobutyronitrile.

Further, 3-methylthiopropionaldehyde obtained by preparation is used for preparing 2-hydroxy-4-methylthiobutyric acid.

The second aspect of the present disclosure is to provide a method for preparing 2-hydroxy-4-methylthiobutyronitrile as an intermediate of 2-hydroxy-4-methylthiobutyric acid, wherein the method comprises: reacting 3-methylthiopropionaldehyde with an excessive amount of hydrocyanic acid to obtain a pre-reaction solution of 2-hydroxy-4-methylthiobutyronitrile; conducting an detection of the content of hydrocyanic acid in the pre-reaction solution of 2-hydroxy-4-methylthiobutyronitrile, and determining the supplementary amount of 3-methylthiopropionaldehyde according to detection results; and mixing and reacting the pre-reaction solution of 2-hydroxy-4-methylthiobutyronitrile with the supplemented 3-methylthiopropionaldehyde to enable a complete reaction of the hydrocyanic acid contained in the pre-reaction solution of 2-hydroxy-4-methylthiobutyronitrile, so as to prepare and obtain 2-hydroxy-4-methylthiobutyronitrile.

Further, the feeding molar ratio of 3-methylthiopropionaldehyde to hydrocyanic acid is 0.95:1 to 0.99:1, preferably 0.97:1 to 0.98:1.

Further, the reaction between 3-methylthiopropionaldehyde and the excessive amount of hydrocyanic acid and the reaction between the supplemented 3-methylthiopropionaldehyde and the pre-reaction solution of 2-hydroxy-4-methylthiobutyronitrile have a reaction temperature of 20 to 80° C., preferably 25 to 45° C.

Further, the method for preparing 2-hydroxy-4-methylthiobutyronitrile as an intermediate of 2-hydroxy-4-methylthiobutyric acid further comprises a step of conducting an online detection of the residual amount of hydrocyanic acid in the obtained 2-hydroxy-4-methylthiobutyronitrile and adjusting the supplementary amount of 3-methylthiopropionaldehyde according to detection results.

Further, an online Raman spectroscopic detection method is employed in the online detection.

Further, the reaction between 3-methylthiopropionaldehyde and the excessive amount of hydrocyanic acid is carried out in a third reactor R3, and the reaction between the supplemented 3-methylthiopropionaldehyde and the pre-reaction solution of 2-hydroxy-4-methylthiobutyronitrile is carried out in a fourth reactor R4.

Further, the third reactor R3 is a recirculation reactor, and the fourth reactor R4 is a plug flow reactor.

Further, the third reactor R3 is a tower reactor or a multi-stage stirred reactor, preferably a tower reactor with baffle plate(s) arranged inside.

Further, an online Raman spectroscopic detector D3 is provided at an outlet of the third reactor R3 for online detection of the content of hydrocyanic acid in the pre-reaction solution of 2-hydroxy-4-methylthiobutyronitrile.

Further, an online Raman spectroscopic detector D4 is provided at an outlet of the fourth reactor R4 for online detection of the content of hydrocyanic acid in 2-hydroxy-4-methylthiobutyronitrile.

Further, a part of the pre-reaction solution of 2-hydroxy-4-methylthiobutyronitrile in the third reactor R3 enters the fourth reactor R4, the rest part is used as circulating materials of the third reactor R3, and the ratio of the amount of materials entering the fourth reactor R4 to the amount of materials used as the circulating materials of the third reactor R3 is 1:5 to 1:30, preferably 1:10 to 1:20.

Further, said 3-methylthiopropionaldehyde is prepared and obtained by using the method provided by the first aspect of the present disclosure.

Further, 2-hydroxy-4-methylthiobutyronitrile obtained by preparation is used for preparing 2-hydroxy-4-methylthiobutyric acid.

The third aspect of the present disclosure is to provide a method for preparing 2-hydroxy-4-methylthiobutyric acid, wherein the method comprises:

step (1): a step of reacting acrolein with methyl mercaptan to prepare 3-methylthiopropionaldehyde;

step (2): a step of reacting 3-methylthiopropionaldehyde with hydrocyanic acid to prepare 2-hydroxy-4-methylthiobutyronitrile; and step (3): a step of hydrating 2-hydroxy-4-methylthiobutyronitrile by using sulfuric acid and then hydrolyzing to prepare 2-hydroxy-4-methylthiobutyric acid.

wherein in steps (1), (2) and (3), the reaction status of the materials is detected online, and the proportions of the materials are controlled according to detection results, so as to enable a complete reaction.

Further, said step (1) comprises:

reacting acrolein with an excessive amount of methyl mercaptan in the presence of a catalyst in a first reactor R1 to form a pre-reaction solution of 3-methylthiopropionaldehyde; conducting an online detection of the content of hemiacetal in the pre-reaction solution of 3-methylthiopropionaldehyde, and determining the supplementary amount of acrolein according to detection results; mixing the pre-reaction solution of 3-methylthiopropionaldehyde with the supplemented acrolein and then allowing the mixture to enter a second reactor R2 to enable a complete reaction of hemiacetal contained in the pre-reaction solution of 3-methylthiopropionaldehyde, so as to prepare and obtain a reaction solution of 3-methylthiopropionaldehyde.

Further, the first reactor R1 is a recirculation reactor selected from a tower reactor or a multi-stage stirred reactor, and is preferably a tower reactor with baffle plate(s) arranged inside.

Further, the feeding molar ratio of acrolein to methyl mercaptan is 0.95:1 to 0.99:1, preferably 0.97:1 to 0.98:1.

Further, a part of the pre-reaction solution of 3-methylthiopropionaldehyde enters the second reactor R2, the rest part is used as circulating materials of the first reactor R1, and the ratio of the amount of materials entering the second reactor R2 to the amount of materials used as the circulating materials of the first reactor R1 is 1:10 to 1:50, preferably 1:15 to 1:30.

Further, said step (1) further comprises a step of conducting an online detection of the residual amount of hemiacetal in 3-methylthiopropionaldehyde and adjusting the supplementary amount of acrolein according to detection results.

Further, the reaction between acrolein and the excessive amount of methyl mercaptan and the reaction between the supplemented acrolein and the pre-reaction solution of 3-methylthiopropionaldehyde have a reaction temperature of 20 to 40° C.

Further, the catalyst is selected from organic bases, inorganic bases, or salts formed by tertiary amines and acids; and the amount of the catalyst is 0.05% to 0.5% and preferably 0.1% to 0.3% of the total mass of acrolein and methyl mercaptan.

Further, the catalyst is a salt formed by a tertiary amine and 2-hydroxy-4-methylthiobutyric acid, wherein the molar ratio of the tertiary amine to 2-hydroxy-4-methylthiobutyric acid is 1.05:1 to 2.0:1, preferably 1.1:1 to 1.5:1; and the tertiary amine is at least one selected from triethylamine, tri-n-propylamine, tri-n-butylamine, triisopropylamine, and N,N-dimethylbenzylamine.

Further, the molar ratio of acrolein to methyl mercaptan in the pre-reaction solution of 3-methylthiopropionaldehyde is 0.95:1 to 0.99:1, preferably 0.97:1 to 0.98:1.

Further, said step (2) comprises:

reacting 3-methylthiopropionaldehyde with an excessive amount of hydrocyanic acid in a third reactor R3 to form a pre-reaction solution of 2-hydroxy-4-methylthiobutyronitrile; conducting an online detection of the content of hydrocyanic acid in the pre-reaction solution of 2-hydroxy-4-methylthiobutyronitrile and determining the supplementary amount of 3-methylthiopropionaldehyde according to detection results; and mixing the pre-reaction solution of 2-hydroxy-4-methylthiobutyronitrile with the supplemented 3-methylthiopropionaldehyde and then allowing the mixture to enter a fourth reactor R4 to enable a complete reaction of hydrocyanic acid contained in 2-hydroxy-4-methylthiobutyronitrile, so as to prepare and obtain 2-hydroxy-4-methylthiobutyronitrile.

Further, the third reactor R3 is selected from a tower reactor or a multi-stage stirred reactor, and is preferably a tower reactor with baffle plate(s) arranged inside.

Further, a part of the pre-reaction solution of 2-hydroxy-4-methylthiobutyronitrile in the third reactor R3 enters the fourth reactor R4, the rest part is used as circulating materials of the third reactor R3, and the ratio of the amount of materials entering the fourth reactor R4 to the amount of materials used as the circulating materials of the third reactor R3 is 1:5 to 1:30, preferably 1:10 to 1:20.

Further, the feeding molar ratio of 3-methylthiopropionaldehyde to hydrocyanic acid is 0.95:1 to 0.99:1, preferably 0.97:1 to 0.98:1.

Further, the reaction between 3-methylthiopropionaldehyde and the excessive amount of hydrocyanic acid and the reaction between the supplemented 3-methylthiopropionaldehyde and the pre-reaction solution of 2-hydroxy-4-methylthiobutyronitrile have a reaction temperature of 25 to 45° C.

Further, said step (2) further comprises a step of conducting an online detection of the residual amount of hydrocyanic acid in 2-hydroxy-4-methylthiobutyronitrile and adjusting the supplementary amount of 3-methylthiopropionaldehyde according to detection results.

Further, said step (3) comprises:

subjecting 2-hydroxy-4-methylthiobutyronitrile to hydration reaction in the presence of sulfuric acid in a hydration reactor R5 to form 2-hydroxy-4-methylthiobutyramide, wherein the residual amount of 2-hydroxy-4-methylthiobutyronitrile in reaction solution is detected online and the amount of sulfuric acid to be used is adjusted according to detection results, so as to enable a complete hydration reaction; and mixing 2-hydroxy-4-methylthiobutyramide with water and then allowing the mixture to enter a hydrolysis reactor R6, so as to prepare 2-hydroxy-4-methylthiobutyric acid via hydrolysis reaction.

Further, the hydration reactor R5 and/or the hydrolysis reactor R6 is a multi-stage stirred reactor with a number of stirring stages of 3 to 20 and preferably 5 to 15.

Further, said step (3) further comprises the following step: adjusting the pH value of 2-hydroxy-4-methylthiobutyric acid to 1 to 2, so as to obtain a neutralized solution of 2-hydroxy-4-methylthiobutyric acid; allowing the neutralized solution of 2-hydroxy-4-methylthiobutyric acid to enter an extraction tower for extraction; and allowing an extract liquor containing 2-hydroxy-4-methylthiobutyric acid to enter a stripping tower, so as to obtain 2-hydroxy-4-methylthiobutyric acid from the bottom of the stripping tower.

Further, the extraction solvent of the neutralized solution of 2-hydroxy-4-methylthiobutyric acid is one selected from methyl isobutyl ketone, butanone, pentanone, hexanone and methyl tert-butyl ether; and the mass ratio of the extraction solvent to the neutralized solution of 2-hydroxy-4-methylthiobutyric acid is 0.3:1 to 3:1, preferably 0.5:1 to 2:1.

Further, the extraction tower is a multi-stage stirred extraction tower with a number of stirring stages of 10 to 30 and preferably 15 to 25.

Further, the stripping tower is a plate tower with a number of plates of 10 to 40 and preferably 15 to 30.

Further, an online Raman spectroscopic detection is employed in the online detection.

The fourth aspect of the present disclosure is to provide a continuous production device for preparing 2-hydroxy-4-methylthiobutyric acid, wherein the continuous production device comprises:

a production device of 3-methylthiopropionaldehyde, a production device of 2-hydroxy-4-methylthiobutyronitrile and a production device of 2-hydroxy-4-methylthiobutyric acid that are sequentially connected;

the production device of 3-methylthiopropionaldehyde comprises a first reactor R1 for forming a pre-reaction solution of 3-methylthiopropionaldehyde and a second reactor R2 for preparing and obtaining 3-methylthiopropionaldehyde, wherein the outlets of the first reactor R1 and the second reactor R2 are respectively provided with a detection device for detecting the content of hemiacetal;

the production device of 2-hydroxy-4-methylthiobutyronitrile comprises a third reactor R3 for forming a pre-reaction solution of 2-hydroxy-4-methylthiobutyronitrile and a fourth reactor R4 for preparing and obtaining 2-hydroxy-4-methylthiobutyronitrile, wherein the outlets of the third reactor R3 and the fourth reactor R4 are respectively provided with a detection device for detecting the content of hydrocyanic acid; and the production device of 2-hydroxy-4-methylthiobutyric acid comprises a hydration reactor R5 for forming 2-hydroxy-4-methylthiobutyramide and a hydrolysis reactor R6 for preparing 2-hydroxy-4-methylthiobutyric acid via hydrolysis reaction, as well as an extraction tower and a stripping tower, wherein the outlet of the hydration reactor R5 is provided with a detection device for detecting the content of 2-hydroxy-4-methylthiobutyronitrile.

Further, said device further comprises a display device for detection results.

Further, the detection device is an online Raman spectroscopic detection device.

Further, the first reactor R1 and the third reactor R3 are both recirculation reactors, which are selected from tower reactors or multi-stage stirred reactors and preferably tower reactors with baffle plate(s) arranged inside.

Further, the second reactor R2 and the fourth reactor R4 are both plug flow reactors.

Further, the hydration reactor R5 and the hydrolysis reactor R6 are both multi-stage stirred reactors with a number of stirring stages of 3 to 20 and preferably 5 to 15.

Further, the extraction tower is a multi-stage stirred extraction tower with a number of stirring stages of 10 to 30 and preferably 15 to 25.

Further, the stripping tower is a plate tower with a number of plates of 10 to 40 and preferably 15 to 30.

Advantageous Effects of the Disclosure

As compared with the prior art, the present disclosure is capable of achieving the following effects.

By adopting the preparation method of the present disclosure, it is possible to conduct online detection for the specific materials (i.e., methyl mercaptan, hydrocyanic acid, and 2-hydroxy-4-methylthiobutyronitrile) involved in the reaction system, reduce the safety risks brought by direct sampling during the production process, and improve the safety of the production process.

By adopting the preparation method of the present disclosure, the reaction efficiencies of various materials such as acrolein, methyl mercaptan, 3-methylthiopropionaldehyde, hydrocyanic acid and 2-hydroxy-4-methylthiobutyronitrile are able to be enhanced, the residual of raw materials in intermediates and products are able to be avoided from the source, and liquid methionine with a high content is prepared and obtained.

By adopting the preparation method of the present disclosure, the proportions of the materials may be strictly controlled such that 3-methylthiopropionaldehyde and 2-hydroxy-4-methylthiobutyronitrile obtained by preparation are almost free of impurities and may directly enter the following processes without being subjected to post-treatment, thereby not only enhancing the production efficiency but also reducing the problem of discharging the "three wastes" generated due to the post-treatment and thus being more environmentally friendly.

By adopting the preparation method and device of the present disclosure, the yield of the product is high, and it is possible to save raw materials and reduce costs.

DESCRIPTION OF REFERENCE SIGNS

Figure 1:
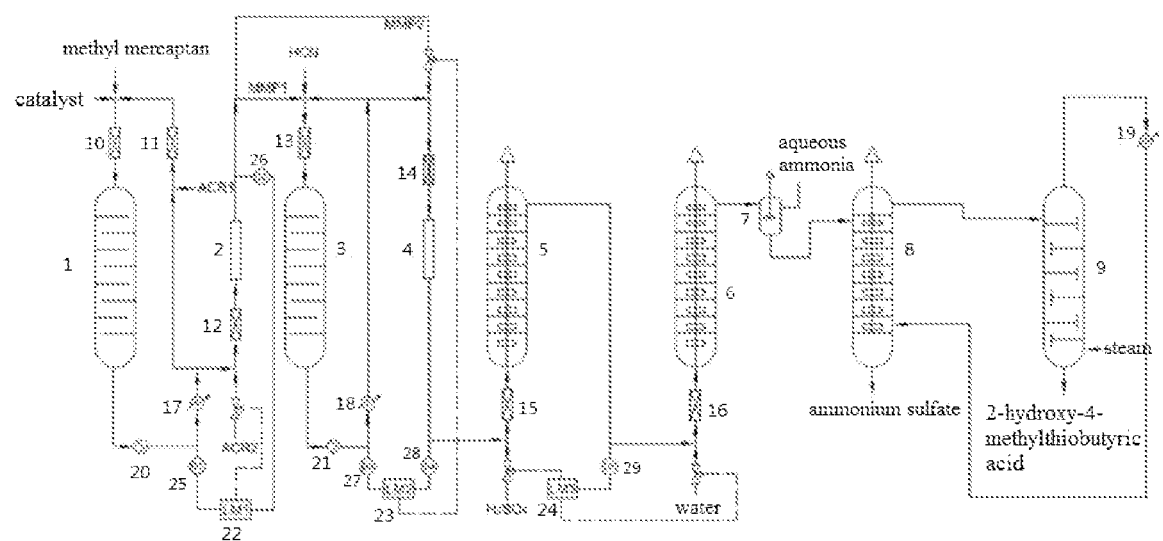
FIG. 1 is a process chart of the continuous preparation of 2-hydroxy-4-methylthiobutyric acid.

1: the first reactor R1
2: the second reactor R2
3: the third reactor R3
4: the fourth reactor R4
5: hydration reactor R5
6: hydrolysis reactor R6
7: neutralization reactor R7
8: extraction tower C1
9: stripping tower C2
10 to 16: static mixers M1 to M7
17 to 19: heat exchangers E1 to E3
20 to 21: circulating pumps P1 to P2
22 to 24: Raman spectrum detecting and processing devices LM1 to LM3
25 to 29: Raman detectors D1 to D5

DETAILED DESCRIPTION

An aspect of the present disclosure is to provide a method for continuously preparing 2-hydroxy-4-methylthiobutyric acid, wherein the method comprises at least the following steps:

a step of subjecting 2-hydroxy-4-methylthiobutyronitrile to hydration reaction in the presence of sulfuric acid to form 2-hydroxy-4-methylthiobutyramide, wherein the residual amount of 2-hydroxy-4-methylthiobutyronitrile in the reaction solution is detected and the amount of sulfuric acid to be used is adjusted according to detection results, so as to enable a complete hydration reaction; and a step of subjecting 2-hydroxy-4-methylthiobutyramide to hydrolysis reaction so as to prepare 2-hydroxy-4-methylthiobutyric acid.

In addition, the present disclosure further provides a method for preparing 2-hydroxy-4-methylthiobutyronitrile, said method comprising:

reacting 3-methylthiopropionaldehyde with an excessive amount of hydrocyanic acid to form a pre-reaction solution of 2-hydroxy-4-methylthiobutyronitrile; detecting the content of hydrocyanic acid in the pre-reaction solution of 2-hydroxy-4-methylthiobutyronitrile and determining the supplementary amount of 3-methylthiopropionaldehyde according to detection results; and mixing the pre-reaction solution of 2-hydroxy-4-methylthiobutyronitrile with the supplemented 3-methylthiopropionaldehyde to enable 3-methylthiopropionaldehyde to react with hydrocyanic acid in an equimolar ratio, so as to prepare and obtain 2-hydroxy-4-methylthiobutyronitrile.

Furthermore, the present disclosure also provides a method for preparing 3-methylthiopropionaldehyde, said method comprising:

reacting acrolein with an excessive amount of methyl mercaptan in the presence of a catalyst to form a pre-reaction solution of 3-methylthiopropionaldehyde; detecting the content of hemiacetal in the pre-reaction solution of 3-methylthiopropionaldehyde and determining the supplementary amount of acrolein according to detection results; and mixing the pre-reaction solution of 3-methylthiopropionaldehyde with the supplemented acrolein to enable acrolein to react with methyl mercaptan in an equimolar ratio, so as to prepare and obtain 3-methylthiopropionaldehyde.

Catalysts commonly used in the art may be used as the catalyst of the present disclosure, including organic bases, inorganic bases, or salts formed by tertiary amines and acids. The organic bases include low-molecular-weight amines, high-molecular-weight amines, or the like. As low-molecular-weight amines, there may be exemplified, for example, amines having 1 to 36 carbon atoms. Preferred low-molecular-weight amines include tri-(C1-C12 alkyl) amines, such as triethylamine and triisopropanolamine; dialkylaralkyl amines, such as dimethylbenzylamine; dialkylaryl amines, such as N, N-dimethylaniline; heterocyclic amines, such as nicotinamide, imidazole, benzimidazole, N—$C_{1-6}$ alkylmorpholine, methylpyridine, pyrazine, or the like. As high-molecular-weight amines, there may be exemplified, for example, polyvinylpyridine, diethylaminoethyl polystyrene, diethylaminomethyl polystyrene, dimethylaminomethyl polystyrene, diethylaminomethyl macroreticular resin, dimethylaminoethyl polystyrene, or the like.

Alkali metal hydroxides, alkali metal cyanides, alkali metal carbonates, alkali metal bicarbonates and the like may be used as inorganic bases. Specifically, there may be exemplified, for example, sodium hydroxide, potassium hydroxide, NaCN, KCN, sodium carbonate, potassium carbonate, sodium bicarbonate, potassium bicarbonate, and the like.

A mixture of a low molecular tertiary amine and an organic acid or an inorganic acid may be used as the mixture of a tertiary amine and an acid, thus being capable of setting pH within a desired range more easily. The organic acids include short-chain fatty acids, organic sulfonic acids, etc. As short-chain fatty acids, for example, acetic acid, formic acid, propionic acid, butyric acid, citric acid and the like are included. As for organic sulfonic acids, there may be exemplified trifluoromethanesulfonic acid and the like. The inorganic acid is preferably sulfuric acid or phosphoric acid.

Said mixture of a tertiary amine and an acid is preferably a salt formed by a tertiary amine and 2-hydroxy-4-methylthiobutyric acid, wherein the molar ratio of the tertiary amine to 2-hydroxy-4-methylthiobutyric acid is 1.05:1 to 2.0:1, preferably 1.1:1 to 1.5:1; and the tertiary amine is at least one selected from triethylamine, tri-n-propylamine, tri-n-butylamine, triisopropylamine, and N,N-dimethylbenzylamine Another aspect of the present disclosure is to provide a method for continuously preparing 2-hydroxy-4-methylthiobutyric acid, comprising:

step (1): a step of reacting acrolein with methyl mercaptan to prepare 3-methylthiopropionaldehyde;

step (2): a step of reacting 3-methylthiopropionaldehyde with hydrocyanic acid to prepare 2-hydroxy-4-methylthiobutyronitrile; and step (3): a step of hydrating 2-hydroxy-4-methylthiobutyronitrile by using sulfuric acid and then hydrolyzing to prepare 2-hydroxy-4-methylthiobutyric acid;

wherein in steps (1), (2) and (3), the reaction status of the materials is detected online, and the proportions of the materials are controlled according to detection results, so as to enable a complete reaction.

A specific embodiment of the present disclosure comprises the following steps.

Step (1): a step of reacting acrolein with methyl mercaptan to prepare 3-methylthiopropionaldehyde The preparation of said 3-methylthiopropionaldehyde is carried out in two continuously operated reactors, wherein the first reactor R1 is a recirculation reactor and the second reactor R2 is a plug flow reactor. The acrolein material ACR1 is first mixed with the circulating materials in the static mixer M2, then the mixture is mixed together with methyl mercaptan and the catalyst in the static mixer M1, and the mixed materials enter the first reactor R1 and are reacted under a condition of 20 to 40° C. to obtain a pre-reaction solution of 3-methylthiopropionaldehyde. After the pre-reaction solution of 3-methylthiopropionaldehyde is cooled, a part of said pre-reaction solution is extracted and supplied to the second reactor R2 for 3-methylthiopropionaldehyde, and the rest part is recycled and used as the circulating materials of the first reactor R1.

In order to ensure an equimolar ratio of methyl mercaptan and acrolein in the second reactor R2, Raman detector D1 is provided at the outlet of the circulating pump P1 at the lower part of the first reactor. The supplementary amount of acrolein ACR2 is determined by determining the content of hemiacetal in the pre-reaction solution of 3-methylthiopropionaldehyde, the supplemented ACR2 and the pre-reaction solution of 3-methylthiopropionaldehyde are mixed in the static mixer M3 and then enter the second reactor R2, and the mixture is further reacted under a condition of 20 to 40° C. to obtain the reaction solution of 3-methylthiopropionaldehyde. Raman detector D2 is provided at the outlet of the second reactor R2. The amount of ACR2 is slightly adjusted by determining the residual amount of hemiacetal in the reaction solution of 3-methylthiopropionaldehyde, so as to ensure a basically complete reaction of hemiacetal.

Step (2): a step of reacting 3-methylthiopropionaldehyde with hydrocyanic acid to prepare 2-hydroxy-4-methylthiobutyronitrile The preparation of said 2-hydroxy-4-methylthiobutyronitrile is also carried out in two continuously operated reactors, wherein the third reactor R3 is a recirculation reactor and the fourth reactor R4 is a plug flow reactor. Most of the material MMP1 in the reaction solution of 3-methylthiopropionaldehyde obtained in the previous step is mixed together with the circulating materials and hydrocyanic acid in the static mixer M4, and the mixed materials enter the third reactor R3 and are reacted under a condition of 25 to 45° C. to obtain a pre-reaction solution of 2-hydroxy-4-methylthiobutyronitrile. A part of the pre-reaction solution of 2-hydroxy-4-methylthiobutyronitrile is extracted and supplied to the fourth reactor R4 for 2-hydroxy-4-methylthiobutyronitrile after being cooled, and the rest part is recycled and used as the circulating materials of the third reactor R3.

In order to ensure an equimolar ratio of hydrocyanic acid and 3-methylthiopropionaldehyde in the fourth reactor R4, Raman detector D3 is provided at the outlet of the circulating pump P2 at the lower part of the first reactor. The supplementary amount of 3-methylthiopropionaldehyde MMP2 is determined by determining the content of hydrocyanic acid in the pre-reaction solution of 2-hydroxy-4-methylthiobutyronitrile. The supplemented MMP2 and the pre-reaction solution of 2-hydroxy-4-methylthiobutyronitrile are mixed in the static mixer M5 and then enter the fourth reactor R4, and the mixture is reacted under a condition of 25 to 45° C. to obtain the reaction solution of 2-hydroxy-4-methylthiobutyronitrile. Raman detector D4 is provided at the outlet of the fourth reactor R4. The amount of MMP2 is slightly adjusted by determining the residual amount of hydrocyanic acid in the reaction solution of 2-hydroxy-4-methylthiobutyronitrile, so as to ensure a basically complete reaction of hydrocyanic acid.

Step (3): a step of hydrating 2-hydroxy-4-methylthiobutyronitrile by using sulfuric acid and then hydrolyzing to prepare 2-hydroxy-4-methylthiobutyric acid The hydrolysis reaction is carried out in two continuous multi-stage stirred reactors connected in series, the hydration reactor R5 is a reactor where 2-hydroxy-4-methylthiobutyronitrile is hydrated to form 2-hydroxy-4-methylthiobutyramide, and the hydrolysis reactor R6 is a reactor where 2-hydroxy-4-methylthiobutyramide is hydrolyzed to synthesize 2-hydroxy-4-methylthiobutyric acid. The reaction solution of 2-hydroxy-4-methylthiobutyronitrile obtained in the previous step and the sulfuric acid solution (70% by weight to 75% by weight) are mixed via the static mixer M6 and then enter the hydration reactor R5, and the mixture is subjected to hydration reaction under a condition of 50 to 70° C. to obtain the reaction solution of 2-hydroxy-4-methylthiobutyramide. This reaction solution and water are mixed together via the static mixer M6 and then enter the hydrolysis reactor R6, and the mixture is heated to 90 to 120° C. and subjected to hydrolysis reaction to obtain the reaction solution of 2-hydroxy-4-methylthiobutyric acid.

In order to ensure a complete hydration reaction, Raman spectroscopic detector D5 is provided at the outlet of the hydration reactor R5. The amount of the sulfuric acid solution is adjusted by determining the residual of 2-hydroxy-4-methylthiobutyronitrile in the reaction solution, and the amount of water entering the hydrolysis reactor R6 is adjusted at the same time, so as to ensure that the hydrolysis reaction is basically complete.

The reaction solution of 2-hydroxy-4-methylthiobutyric acid obtained by the above-mentioned hydrolysis reaction is supplied to the continuous neutralization reactor R7 and is adjusted with ammonia to reach a pH value of 1 to 2, so as to obtain the neutralized solution of 2-hydroxy-4-methylthiobutyric acid. Then, said neutralized solution enters the upper part of the multi-stage extraction tower C1, the solvent enters the lower part of the extraction tower C1, and countercurrent extraction is carried out under a condition of 30 to 50° C. An extract liquor containing 2-hydroxy-4-methylthiobutyric acid is obtained from the top of the extraction tower C1, and an ammonium sulfate solution is obtained from the bottom. The extract liquor containing 2-hydroxy-4-methylthiobutyric acid enters the upper part of the stripping tower C2, the steam is introduced into the bottom to conduct steam stripping, and the solvent vapor obtained from the top of the stripping tower may be directly applied to the extraction tower C1 after being condensed by the condenser E3. The product 2-hydroxy-4-methylthiobutyric acid is obtained from the bottom of the stripping tower.

The method for continuously preparing 2-hydroxy-4-methylthiobutyric acid provided by the present disclosure is capable of solving the problem existing in the prior art that the detection is unable to be conducted online. In a preferred technical solution of the present disclosure, Raman spectroscopic detection is employed in combination with the process control, which enables well control of the proportions of the raw materials of the reaction and thus achieves the purposes of reducing the consumption of raw materials, reducing by-products, reducing the residual of raw materials and intermediates, and improving operational safety and process stability.

By testing the Raman spectroscopic signals of the reactants and intermediates in each step of the reaction, the inventors have discovered that, when methyl mercaptan is reacted with acrolein, if 3-methylthiopropionaldehyde (MMP) is used as the solvent, methyl mercaptan will react with MMP to form hemiacetal, and its reaction formula is as follows:

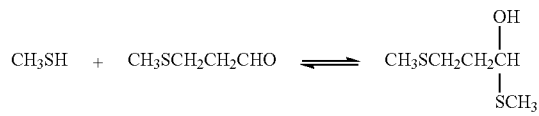

Figure 2:
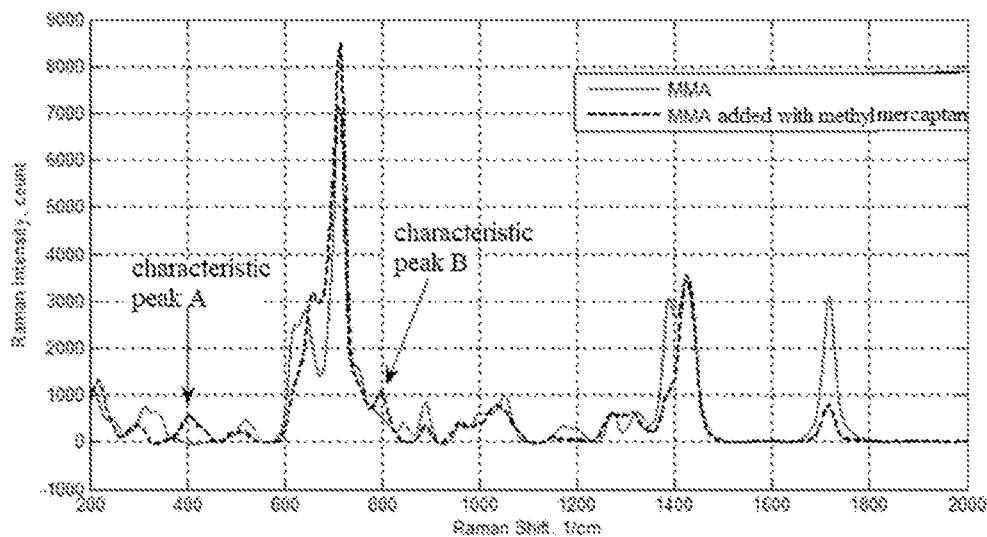
FIG. 2 shows the comparison between the Raman spectrum of 3-methylthiopropionaldehyde and the Raman spectra of hemiacetal of 3-methylthiopropionaldehyde and methyl mercaptan.

Hemiacetal formed by the reaction has characteristic absorption peaks in the Raman spectrum, and the characteristic absorption peaks have maximum absorption at a wave number of 400 cm$^{-1}$ (see FIG. 2, characteristic peak A), and the content of methyl mercaptan in the reaction solution may be determined accurately by using this absorption peak. Accordingly, in the present disclosure, the synthesis of MMP is carried out in two reactors connected in series. The product MMP is used as the reaction medium in the first reactor, most of the acrolein is first reacted with an excessive amount of methyl mercaptan, the process parameters of the reaction is adjusted to enable a basically complete reaction of acrolein, and the excess methyl mercaptan is reacted with MMP to form hemiacetal. The content of methyl mercaptan may be calculated and obtained by determining the content of hemiacetal in the pre-reaction solution at the outlet of the first reactor, then acrolein of which the amount is required by the stoichiometric ratio is added additionally at the inlet of the second reactor, and hemiacetal is basically reacted completely in the second reactor.

Figure 3:
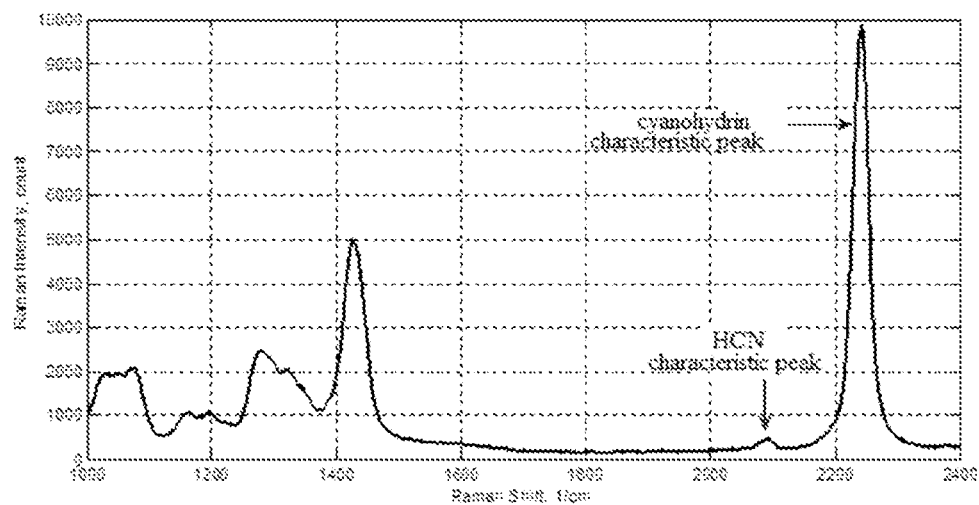
FIG. 3 is the Raman spectrum of the mixture of 2-hydroxy-4-methylthiobutyronitrile and hydrocyanic acid.

The same idea is adopted upon reacting MMP with hydrocyanic acid to form 2-hydroxy-4-methylthiobutyronitrile. It has been found by the research that hydrocyanic acid and 2-hydroxy-4-methylthiobutyronitrile have characteristic absorption peaks at wave numbers of about 2080 cm$^{-1}$ and about 2240 cm$^{-1}$, respectively (see FIG. 3) (the characteristic peak of cyanohydrin indicated in the figure is the characteristic peak of 2-hydroxy-4-methylthiobutyronitrile), and the content of hydrocyanic acid may be determined by the relative size of the two absorption peaks. Therefore, 2-hydroxy-4-methylthiobutyronitrile is used as the reaction medium, most of the MMP is first reacted with an excessive amount of hydrocyanic acid in the third reactor, and the process parameters of the reaction is adjusted to enable a basically complete reaction of MMP. The content of hydrocyanic acid in the pre-reaction solution at the outlet of the third reactor is determined, then MMP of which the amount is required by the stoichiometric ratio is added additionally at the inlet of the fourth reactor, and hydrocyanic acid is basically reacted completely in the fourth reactor.

Figure 4:
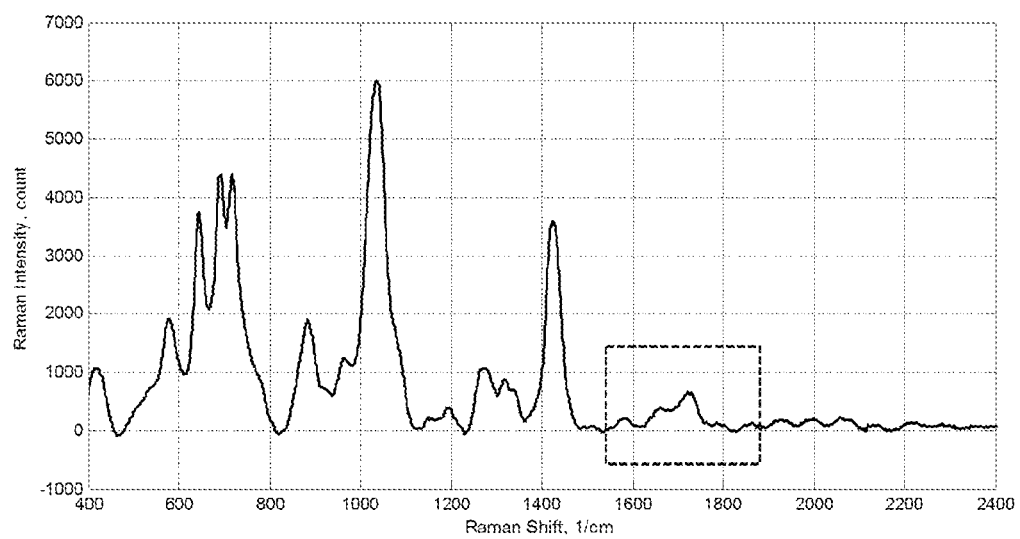
FIG. 4 is the Raman spectrum of 2-hydroxy-4-methylthiobutyramide.

Since 2-hydroxy-4-methylthiobutyronitrile is unstable, in order to ensure that the by-products are reduced as far as possible during hydrolysis reaction, there is a need to synthesize 2-hydroxy-4-methylthiobutyramide via sufficient hydration at a relatively low temperature in sulfuric acid with a relatively high concentration. For this reason, online Raman spectroscopy is employed in the present disclosure to monitor the hydration process of 2-hydroxy-4-methylthiobutyronitrile. By monitoring whether the characteristic absorption peak of 2-hydroxy-4-methylthiobutyronitrile (wave number: 2240 cm$^{-1}$) is completely converted into the characteristic absorption peak of amide (wave number: 1730 cm$^{-1}$, see FIG. 4) at the outlet of the hydration reactor, the degree of the hydration reaction is determined, and the feeding amount of sulfuric acid and the amount of water in the subsequent hydrolysis reaction are adjusted accordingly.

Another aspect of the present disclosure is to provide a continuous production device for preparing 2-hydroxy-4-methylthiobutyric acid comprising:
a production device of 3-methylthiopropionaldehyde, a production device of 2-hydroxy-4-methylthiobutyronitrile and a production device of 2-hydroxy-4-methylthiobutyric acid that are sequentially connected;
the production device of 3-methylthiopropionaldehyde comprises the first reactor (R1) for forming a pre-reaction solution of 3-methylthiopropionaldehyde and the second reactor (R2) for preparing and obtaining 3-methylthiopropionaldehyde, wherein the outlets of the first reactor (R1) and the second reactor (R2) are respectively provided with a detection device for detecting the content of hemiacetal;

the production device of 2-hydroxy-4-methylthiobutyronitrile comprises the third reactor (R3) for forming a pre-reaction solution of 2-hydroxy-4-methylthiobutyronitrile and the fourth reactor (R4) for preparing and obtaining 2-hydroxy-4-methylthiobutyronitrile, wherein the outlets of the third reactor (R3) and the fourth reactor (R4) are respectively provided with a detection device for detecting the content of hydrocyanic acid; and the production device of 2-hydroxy-4-methylthiobutyric acid comprises the hydration reactor (R5) for forming a 2-hydroxy-4-methylthiobutyramide and the hydrolysis reactor (R6) for preparing 2-hydroxy-4-methylthiobutyric acid via hydrolysis reaction, as well as an extraction tower and a stripping tower, wherein the outlet of the hydration reactor (R5) is provided with a detection device for detecting the content of 2-hydroxy-4-methylthiobutyronitrile.

Specific equipments such as the reactor, the extraction tower, the stripping tower, the static mixer, the heat exchanger, the circulating pump and the detector that are specifically used in the present disclosure may be obtained commercially.

The detection device of the present disclosure is preferably a Raman spectrum detection device comprising a Raman spectroscopic detector (sometimes also described as Raman detector, for example, Raman detectors D1 to D5) and a Raman spectrum detecting and processing device (for example, LM1 to LM3). Said Raman spectrum detecting and processing device is used for collecting and processing the Raman spectroscopic signals collected by the Raman detector and forming a Raman spectrum. Any of said Raman detectors is connected to a Raman spectrum detecting and processing device (several Raman detectors may be connected to a single Raman spectrum detecting and processing device). Preferably, the connection between the Raman detectors and the Raman spectrum detecting and processing devices is selected according to the stage of reaction. In some specific embodiments, Raman detectors D1 and D2 are connected to Raman spectrum detecting and processing device LM1, Raman detectors D3 and D4 are connected to Raman spectrum detecting and processing device LM2, and Raman detector D5 is connected to Raman spectrum detecting and processing device LM3.

As an example of the present disclosure, the first reactor (R1) and the third reactor (R3) are both recirculation reactors, which are selected from conventional tower reactors or multi-stage stirred reactors in the art and preferably tower reactors with baffle plate(s) arranged inside. The second reactor (R2) and the fourth reactor (R4) are both plug flow reactors; the hydration reactor (R5) and the hydrolysis reactor (R6) are both multi-stage stirred reactors with a number of stirring stages of 3 to 20 and preferably 5 to 15; the extraction tower is a multi-stage stirred extraction tower with a number of stirring stages of 10 to 30 and preferably 15 to 25; and the stripping tower is a plate tower with a number of plates of 10 to 40 and preferably 15 to 30.

In the present specification, the wording "comprising" or "containing" should be understood as an open, non-exclusive meaning, that is, "including but not limited to".

In the present disclosure, a percentage refers to a mass percentage, unless otherwise specified.

The technical solutions of the present disclosure are explained more specifically below in conjunction with Examples.

Example 1

The synthesis of 2-hydroxy-4-methylthiobutyric acid was carried out according to the process as shown in FIG. 1, wherein:

R1 had a volume of 1 $m^3$ and was a straight pipe with an inner diameter of 0.6 m, a length of 3.55 m and 10 baffle plates arranged inside;

R2 had a volume of 0.2 $m^3$ and was a straight pipe with an inner diameter of 0.3 m and a length of 2.85 m;

R3 had a volume of 0.5 $m^3$ and was a straight pipe with an inner diameter of 0.5 m, a length of 2.55 m and 8 baffle plates arranged inside;

R4 had a volume of 0.1 $m^3$ and was a straight pipe with an inner diameter of 0.2 m and a length of 3.20 m;

R5 had a volume of 1 $m^3$ and was a straight pipe with an inner diameter of 0.6 m, a length of 3.55 m and 10 stages of stirring arranged inside;

R6 had a volume of 2 $m^3$ and was a straight pipe with an inner diameter of 0.8 m, a length of 4.00 m and 10 stages of stirring arranged inside;

R7 had a volume of 0.2 $m^3$ and was a reaction kettle with a stirrer arranged inside; C1 was an extraction tower with a diameter of 1 m and 20 stages of stirring arranged inside; and C2 was a plate tower with a diameter of 1 m and 25 sieve plates arranged inside.

(1) Preparation of 3-methylthiopropionaldehyde

The acrolein material ACR1 was first mixed with the circulating materials in the static mixer M2 at 545 Kg/hour, then the mixture was mixed together with methyl mercaptan (480 Kg/hour) and the catalyst (triethylamine and 2-hydroxy-4-methylthiobutyric acid were mixed at a molar ratio of 1.2:1) (1 Kg/hour) in the static mixer M1, and the mixed materials entered the first reactor R1 and were reacted under a condition of 27 to 30° C. to obtain a pre-reaction solution of 3-methylthiopropionaldehyde. After the pre-reaction solution of 3-methylthiopropionaldehyde was cooled, said pre-reaction solution (about 1026 Kg/hour) was extracted and supplied to the second reactor R2 for 3-methylthiopropionaldehyde, and the amount of materials used as the circulating materials of the first reactor R1 was about 20000 Kg/hour.

The supplementary amount of acrolein ACR2 was determined as 16 Kg/hour by using Raman detector D1 to determine the content of hemiacetal in the pre-reaction solution of 3-methylthiopropionaldehyde. The supplemented ACR2 and the pre-reaction solution of 3-methylthiopropionaldehyde were mixed in the static mixer M3 and then entered the second reactor R2, and the mixture was further reacted under a condition of 27 to 28° C. to obtain the reaction solution of 3-methylthiopropionaldehyde. The residual amount of hemiacetal in the reaction solution of 3-methylthiopropionaldehyde was determined by Raman detector D2 to confirm a basically complete reaction of hemiacetal.

(2) Preparation of 2-hydroxy-4-methylthiobutyronitrile

Most of the material MMP1 in the reaction solution of 3-methylthiopropionaldehyde obtained in the previous step was mixed together with the circulating materials and hydrocyanic acid (270 Kg/hour) in the static mixer M4 at 1010 Kg/hour, and the mixed materials entered the third reactor R3 and were reacted under a condition of 33 to 35° C. to obtain a pre-reaction solution of 2-hydroxy-4-methylthiobutyronitrile. The pre-reaction solution of 2-hydroxy-4-methylthiobutyronitrile was supplied to the fourth reactor R4 for 2-hydroxy-4-methylthiobutyronitrile at 1280

Kg/hour after being cooled, and the amount of materials used as the circulating materials of the second reactor R3 was 25600 Kg/hour.

The supplementary amount of 3-methylthiopropionaldehyde MMP2 was determined as 32 Kg/hour by using Raman detector D3 to determine the content of hydrocyanic acid in the pre-reaction solution of 2-hydroxy-4-methylthiobutyronitrile. The supplemented MMP2 and the pre-reaction solution of 2-hydroxy-4-methylthiobutyronitrile were mixed in the static mixer M5 and then entered the fourth reactor R4, and the mixture was reacted under a condition of 33 to 34° C. to obtain the reaction solution of 2-hydroxy-4-methylthiobutyronitrile. The residual amount of hydrocyanic acid in the reaction solution of 2-hydroxy-4-methylthiobutyronitrile was determined by Raman detector D4 to confirm a basically complete reaction of hydrocyanic acid.

(3) Preparation of 2-hydroxy-4-methylthiobutyric acid

The reaction solution of 2-hydroxy-4-methylthiobutyronitrile obtained in the previous step and the sulfuric acid solution (1680 Kg/hour, 70% by weight) were mixed via the static mixer M6 and then entered the hydration reactor R5, and the mixture was subjected to hydration reaction under a condition of 55 to 60° C. to obtain the reaction solution of 2-hydroxy-4-methylthiobutyramide. This reaction solution and water (2300 Kg/hour) were mixed together via the static mixer M6 and then entered the hydrolysis reactor R6, and the mixture was heated to 100 to 105° C. and subjected to hydrolysis reaction to obtain the reaction solution of 2-hydroxy-4-methylthiobutyric acid.

The hydration reaction process was fully carried out. The amount of the sulfuric acid solution was adjusted by using Raman spectroscopic detector D5 to determine the residual of 2-hydroxy-4-methylthiobutyronitrile in the reaction solution, and the amount of water entering the hydrolysis reactor R6 was adjusted at the same time, so as to ensure that the hydrolysis reaction was basically complete.

The reaction solution of 2-hydroxy-4-methylthiobutyric acid obtained by the above-mentioned hydrolysis reaction was supplied to the continuous neutralization reactor R7 and was adjusted with ammonia to reach a pH value of 1.5, so as to obtain the neutralized solution of 2-hydroxy-4-methylthiobutyric acid. Then, said neutralized solution entered the upper part of the multi-stage extraction tower C1, methyl isobutyl ketone as a solvent entered the lower part of the extraction tower C1 at 5000 Kg/hour, and countercurrent extraction was carried out under a condition of 35 to 40° C. An extract liquor containing 2-hydroxy-4-methylthiobutyric acid was obtained from the top of the tower, and an ammonium sulfate solution was obtained from the bottom at 3630 Kg/hour. The extract liquor containing 2-hydroxy-4-methylthiobutyric acid entered the upper part of the stripping tower C2, the steam was introduced into the bottom to conduct steam stripping, and the solvent vapor obtained from the top of the stripping tower could be directly applied to the extraction tower C1 after being condensed by the condenser E3. The product 2-hydroxy-4-methylthiobutyric acid was obtained from the bottom of the stripping tower at 1685 Kg/hour, and said product had a content of 88.92% and a yield of 99.71% in terms of acrolein.

Example 2

The synthesis of 2-hydroxy-4-methylthiobutyric acid was carried out according to the process as shown in FIG. 1, wherein:

R1 had a volume of 1 m³ and was a straight pipe with an inner diameter of 0.6 m, a length of 3.55 m and 10 baffle plates arranged inside;

R2 had a volume of 0.2 m³ and was a straight pipe with an inner diameter of 0.3 m and a length of 2.85 m;

R3 had a volume of 0.5 m³ and was a straight pipe with an inner diameter of 0.5 m, a length of 2.55 m and 8 baffle plates arranged inside;

R4 had a volume of 0.1 m³ and was a straight pipe with an inner diameter of 0.2 m and a length of 3.20 m;

R5 had a volume of 1 m³ and was a straight pipe with an inner diameter of 0.6 m, a length of 3.55 m and 20 stages of stirring arranged inside;

R6 had a volume of 2 m³ and was a straight pipe with an inner diameter of 0.8 m, a length of 4.00 m and 20 stages of stirring arranged inside;

R7 had a volume of 0.2 m³ and was a reaction kettle with a stirrer arranged inside; C1 was an extraction tower with a diameter of 1 m and 30 stages of stirring arranged inside; and C2 was a plate tower with a diameter of 1 m and 10 sieve plates arranged inside.

(1) Preparation of 3-methylthiopropionaldehyde

The acrolein material ACR1 was first mixed with the circulating materials in the static mixer M2 at 1100 Kg/hour, then the mixture was mixed together with methyl mercaptan (960 Kg/hour) and the catalyst (the molar ratio of tributylamine to 2-hydroxy-4-methylthiobutyric acid was 1.05:1) (1 Kg/hour) in the static mixer M1, and the mixed materials entered the first reactor R1 and were reacted under a condition of 35 to 40° C. to obtain a pre-reaction solution of 3-methylthiopropionaldehyde. After the pre-reaction solution of 3-methylthiopropionaldehyde was cooled, said pre-reaction solution (about 2061 Kg/hour) was extracted and supplied to the second reactor R2 for 3-methylthiopropionaldehyde, and the amount of materials used as the circulating materials of the first reactor R1 was about 21000 Kg/hour.

The supplementary amount of acrolein ACR2 was determined as 23 Kg/hour by using Raman detector D1 to determine the content of hemiacetal in the pre-reaction solution of 3-methylthiopropionaldehyde. The supplemented ACR2 and the pre-reaction solution of 3-methylthiopropionaldehyde were mixed in the static mixer M3 and then entered the second reactor R2, and the mixture was further reacted under a condition of 35 to 36° C. to obtain the reaction solution of 3-methylthiopropionaldehyde. The residual amount of hemiacetal in the reaction solution of 3-methylthiopropionaldehyde was determined by Raman detector D2 to confirm a basically complete reaction of hemiacetal.

(2) Preparation of 2-hydroxy-4-methylthiobutyronitrile

Most of the material MMP1 in the reaction solution of 3-methylthiopropionaldehyde obtained in the previous step was mixed together with the circulating materials and hydrocyanic acid (540 Kg/hour) in the static mixer M4 at 2063 Kg/hour, and the mixed materials entered the third reactor R3 and were reacted under a condition of 40 to 45° C. to obtain a pre-reaction solution of 2-hydroxy-4-methylthiobutyronitrile. The pre-reaction solution of 2-hydroxy-4-methylthiobutyronitrile was supplied to the fourth reactor R4 for 2-hydroxy-4-methylthiobutyronitrile at 2603 Kg/hour after being cooled, and the amount of materials used as the circulating materials of the second reactor R3 was 13100 Kg/hour.

The supplementary amount of 3-methylthiopropionaldehyde MMP2 was determined as 21 Kg/hour by using Raman detector D3 to determine the content of hydrocyanic acid in the pre-reaction solution of 2-hydroxy-4-methylthiobutyronitrile. The supplemented MMP2 and the pre-reaction solution of 2-hydroxy-4-methylthiobutyronitrile were mixed in the static mixer M5 and then entered the fourth reactor R4, and the mixture was reacted under a condition of 40 to 41° C. to obtain the reaction solution of 2-hydroxy-4-methylthiobutyronitrile. The residual amount of hydrocyanic acid in the reaction solution of 2-hydroxy-4-methylthiobutyronitrile was determined by Raman detector D4 to confirm a basically complete reaction of hydrocyanic acid.

(3) Preparation of 2-hydroxy-4-methylthiobutyric acid

The reaction solution of 2-hydroxy-4-methylthiobutyronitrile obtained in the previous step and the sulfuric acid solution (2613 Kg/hour, 75% by weight) were mixed via the static mixer M6 and then entered the hydration reactor R5, and the mixture was subjected to hydration reaction under a condition of 65 to 70° C. to obtain the reaction solution of 2-hydroxy-4-methylthiobutyramide. This reaction solution and water (3750 Kg/hour) were mixed together via the static mixer M6 and then entered the hydrolysis reactor R6, and the mixture was heated to 115 to 120° C. and subjected to hydrolysis reaction to obtain the reaction solution of 2-hydroxy-4-methylthiobutyric acid.

The hydration reaction process was fully carried out. The amount of the sulfuric acid solution was adjusted by using Raman spectroscopic detector D5 to determine the residual of 2-hydroxy-4-methylthiobutyronitrile in the reaction solution, and the amount of water entering the hydrolysis reactor R6 was adjusted at the same time, so as to ensure that the hydrolysis reaction was basically complete.

The reaction solution of 2-hydroxy-4-methylthiobutyric acid obtained by the above-mentioned hydrolysis reaction was supplied to the continuous neutralization reactor R7 and was adjusted with aqueous ammonia to reach a pH value of 2, so as to obtain the neutralized solution of 2-hydroxy-4-methylthiobutyric acid. Then, said neutralized solution entered the upper part of the multi-stage extraction tower C1, methyl tert-butyl ether as a solvent entered the lower part of the extraction tower C1 at 2800 Kg/hour, and countercurrent extraction was carried out under a condition of 45 to 50° C. An extract liquor containing 2-hydroxy-4-methylthiobutyric acid was obtained from the top of the tower, and an ammonium sulfate solution was obtained from the bottom at 5955 Kg/hour. The extract liquor containing 2-hydroxy-4-methylthiobutyric acid entered the upper part of the stripping tower C2, the steam was introduced into the bottom to conduct steam stripping, and the solvent vapor obtained from the top of the stripping tower could be directly applied to the extraction tower C1 after being condensed by the condenser E3. The product 2-hydroxy-4-methylthiobutyric acid was obtained from the bottom of the stripping tower at 3372 Kg/hour, and said product had a content of 88.85% and a yield of 99.60% in terms of acrolein.

Example 3

The synthesis of 2-hydroxy-4-methylthiobutyric acid was carried out according to the process as shown in FIG. 1, wherein:

R1 had a volume of 1 m³ and was a straight pipe with an inner diameter of 0.6 m, a length of 3.55 m and 10 baffle plates arranged inside;

R2 had a volume of 0.2 m³ and was a straight pipe with an inner diameter of 0.3 m and a length of 2.85 m;

R3 had a volume of 0.5 m³ and was a straight pipe with an inner diameter of 0.5 m, a length of 2.55 m and 8 baffle plates arranged inside;

R4 had a volume of 0.1 m³ and was a straight pipe with an inner diameter of 0.2 m and a length of 3.20 m;

R5 had a volume of 1 m³ and was a straight pipe with an inner diameter of 0.6 m, a length of 3.55 m and 3 stages of stirring arranged inside;

R6 had a volume of 2 m³ and was a straight pipe with an inner diameter of 0.8 m, a length of 4.00 m and 3 stages of stirring arranged inside;

R7 had a volume of 0.2 m³ and was a reaction kettle with a stirrer arranged inside; C1 was an extraction tower with a diameter of 1 m and 10 stages of stirring arranged inside; and C2 was a plate tower with a diameter of 1 m and 40 sieve plates arranged inside.

(1) Preparation of 3-methylthiopropionaldehyde

The acrolein material ACR1 was first mixed with the circulating materials in the static mixer M2 at 266 Kg/hour, then the mixture was mixed together with methyl mercaptan (240 Kg/hour) and the catalyst (the molar ratio of N,N-dimethylbenzylamine to 2-hydroxy-4-methylthiobutyric acid was 2:1) (2 Kg/hour) in the static mixer M1, and the mixed materials entered the first reactor R1 and were reacted under a condition of 20 to 22° C. to obtain a pre-reaction solution of 3-methylthiopropionaldehyde. After the pre-reaction solution of 3-methylthiopropionaldehyde was cooled, said pre-reaction solution (about 508 Kg/hour) was extracted and supplied to the second reactor R2 for 3-methylthiopropionaldehyde, and the amount of materials used as the circulating materials of the first reactor R1 was about 25000 Kg/hour.

The supplementary amount of acrolein ACR2 was determined as 15 Kg/hour by using Raman detector D1 to determine the content of hemiacetal in the pre-reaction solution of 3-methylthiopropionaldehyde. The supplemented ACR2 and the pre-reaction solution of 3-methylthiopropionaldehyde were mixed in the static mixer M3 and then entered the second reactor R2, and the mixture was further reacted under a condition of 20 to 21° C. to obtain the reaction solution of 3-methylthiopropionaldehyde. The residual amount of hemiacetal in the reaction solution of 3-methylthiopropionaldehyde was determined by Raman detector D2 to confirm a basically complete reaction of hemiacetal.

(2) Preparation of 2-hydroxy-4-methylthiobutyronitrile

Most of the material MMP1 in the reaction solution of 3-methylthiopropionaldehyde obtained in the previous step was mixed together with the circulating materials and hydrocyanic acid (135 Kg/hour) in the static mixer M4 at 497 Kg/hour, and the mixed materials entered the third reactor R3 and were reacted under a condition of 25 to 27° C. to obtain a pre-reaction solution of 2-hydroxy-4-methylthiobutyronitrile. The pre-reaction solution of 2-hydroxy-4-methylthiobutyronitrile was supplied to the fourth reactor R4 for 2-hydroxy-4-methylthiobutyronitrile at 632 Kg/hour after being cooled, and the amount of materials used as the circulating materials of the second reactor R3 was 18900 Kg/hour.

The supplementary amount of 3-methylthiopropionaldehyde MMP2 was determined as 26 Kg/hour by using Raman detector D3 to determine the content of hydrocyanic acid in the pre-reaction solution of 2-hydroxy-4-methylthiobutyronitrile. The supplemented MMP2 and the pre-reaction solution of 2-hydroxy-4-methylthiobutyronitrile were mixed in the static mixer M5 and then entered the fourth reactor R4, and the mixture was reacted under a condition of 25 to 26° C. to obtain the reaction solution of 2-hydroxy-4-methylthiobutyronitrile. The residual amount of hydrocyanic acid in the reaction solution of 2-hydroxy-4-methylthiobutyronitrile was determined by Raman detector D4 to confirm a basically complete reaction of hydrocyanic acid.

(3) Preparation of 2-hydroxy-4-methylthiobutyric acid

The reaction solution of 2-hydroxy-4-methylthiobutyronitrile obtained in the previous step and the sulfuric acid solution (1360 Kg/hour, 72% by weight) were mixed via the static mixer M6 and then entered the hydration reactor R5, and the mixture was subjected to hydration reaction under a condition of 50 to 55° C. to obtain the reaction solution of 2-hydroxy-4-methylthiobutyramide. This reaction solution and water (1700 Kg/hour) were mixed together via the static mixer M6 and then entered the hydrolysis reactor R6, and the mixture was heated to 90 to 95° C. and subjected to hydrolysis reaction to obtain the reaction solution of 2-hydroxy-4-methylthiobutyric acid.

The hydration reaction process was fully carried out. The amount of the sulfuric acid solution was adjusted by using Raman spectroscopic detector D5 to determine the residual of 2-hydroxy-4-methylthiobutyronitrile in the reaction solution, and the amount of water entering the hydrolysis reactor R6 was adjusted at the same time, so as to ensure that the hydrolysis reaction was basically complete.

The reaction solution of 2-hydroxy-4-methylthiobutyric acid obtained by the above-mentioned hydrolysis reaction was supplied to the continuous neutralization reactor R7 and was adjusted with ammonia to reach a pH value of 1, so as to obtain the neutralized solution of 2-hydroxy-4-methylthiobutyric acid. Then, said neutralized solution entered the upper part of the multi-stage extraction tower C1, butanone as a solvent entered the lower part of the extraction tower C1 at 11900 Kg/hour, and countercurrent extraction was carried out under a condition of 30 to 35° C. An extract liquor containing 2-hydroxy-4-methylthiobutyric acid was obtained from the top of the tower, and an ammonium sulfate solution was obtained from the bottom at 3130 Kg/hour. The extract liquor containing 2-hydroxy-4-methylthiobutyric acid entered the upper part of the stripping tower C2, the steam was introduced into the bottom to conduct steam stripping, and the solvent vapor obtained from the top of the stripping tower could be directly applied to the extraction tower C1 after being condensed by the condenser E3. The product 2-hydroxy-4-methylthiobutyric acid was obtained from the bottom of the stripping tower at 843 Kg/hour, and said product had a content of 88.97% and a yield of 99.65% in terms of acrolein.

The above examples are illustrative for the technical solutions of the present disclosure, and are not intended to limit the scope of the present disclosure to the above examples. Therefore, the protection scope claimed by the present disclosure is not limited by the above examples, and any technical solution achieved by equivalent replacement falls within the protection scope of the present disclosure.

What is claimed is:

1. A method for preparing 2-hydroxy-4-methylthiobutyric acid, wherein the method comprises:
    step (1): a step of reacting acrolein with methyl mercaptan to prepare 3-methylthiopropionaldehyde;
    step (2): a step of reacting 3-methylthiopropionaldehyde with hydrocyanic acid to prepare 2-hydroxy-4-methylthiobutyronitrile comprising reacting 3-methylthiopropionaldehyde with an excessive amount of hydrocyanic acid in a third reactor R3 to form a pre-reaction solution of 2-hydroxy-4-methylthiobutyronitrile; conducting an online detection of a content of hydrocyanic acid in the pre-reaction solution of 2-hydroxy-4-methylthiobutyronitrile and determining a supplementary amount of 3-methylthiopropionaldehyde according to detection results; and mixing the pre-reaction solution of 2-hydroxy-4-methylthiobutyronitrile with the supplemented 3-methylthiopropionaldehyde and then allowing the mixture to enter a fourth reactor R4 to enable a complete reaction of hydrocyanic acid contained in 2-hydroxy-4-methylthiobutyronitrile, so as to prepare and obtain 2-hydroxy-4-methylthiobutyronitrile; and
    step (3): a step of hydrating 2-hydroxy-4-methylthiobutyronitrile by using sulfuric acid and then hydrolyzing to prepare 2-hydroxy-4-methylthiobutyric acid;
    wherein in at least one of steps (1), (2) and (3), the reaction status of materials is detected online, and proportions of the materials are controlled according to detection results, so as to enable a complete reaction, and
    wherein the third reactor R3 and the fourth reactor R4 are free of catalyst for reacting 3-methylthiopropionaldehyde and hydrocyanic acid.

2. The method according to claim 1, wherein said step (1) comprises:
    reacting acrolein with an excessive amount of methyl mercaptan in the presence of a catalyst in a first reactor R1 to form a pre-reaction solution of 3-methylthiopropionaldehyde; conducting an online detection of a content of hemiacetal in the pre-reaction solution of 3-methylthiopropionaldehyde, and determining a supplementary amount of acrolein according to detection results; mixing the pre-reaction solution of 3-methylthiopropionaldehyde with the supplemented acrolein and then allowing the mixture to enter a second reactor R2 to enable a complete reaction of hemiacetal contained in the pre-reaction solution of 3-methylthiopropionaldehyde, so as to prepare and obtain a reaction solution of 3-methylthiopropionaldehyde.

3. The method according to claim 2, wherein the first reactor R1 is a recirculation reactor selected from a tower reactor or a multi-stage stirred reactor.

4. The method according to claim 2, wherein a feeding molar ratio of acrolein to methyl mercaptan is 0.95:1 to 0.99:1.

5. The method according to claim 2, wherein a part of the pre-reaction solution of 3-methylthiopropionaldehyde enters the second reactor R2, the rest part is used as circulating materials of the first reactor R1, and a ratio of the amount of materials entering the second reactor R2 to the amount of materials used as the circulating materials of the first reactor R1 is 1:10 to 1:50.

6. The method according to claim 2, wherein said step (1) further comprises a step of conducting an online detection of a residual amount of hemiacetal in 3-methylthiopropionaldehyde and adjusting the supplementary amount of acrolein according to detection results.

7. The method according to claim 2, wherein a reaction between acrolein and the excessive amount of methyl mercaptan and a reaction between the supplemented acrolein and the pre-reaction solution of 3-methylthiopropionaldehyde have a reaction temperature of 20 to 40° C.; a molar ratio of acrolein to methyl mercaptan in the pre-reaction solution of 3-methylthiopropionaldehyde is 0.95:1 to 0.99:1.

8. The method according to claim 1, wherein the step (1) further comprises contacting a catalyst with the acrolein and the methyl mercaptan to prepare 3-methylthiopropionaldehyde, and wherein the catalyst is selected from organic bases, inorganic bases, or salts formed by tertiary amines and acids; and an amount of the catalyst is 0.05% to 0.5% of a total mass of acrolein and methyl mercaptan.

9. The method according to claim 1, wherein the third reactor R3 is selected from a tower reactor or a multi-stage stirred reactor; a part of the pre-reaction solution of 2-hydroxy-4-methylthiobutyronitrile in the third reactor R3 enters the fourth reactor R4, the rest part is used as circulating materials of the third reactor R3, and a ratio of the amount of materials entering the fourth reactor R4 to the amount of materials used as the circulating materials of the third reactor R3 is 1:5 to 1:30.

10. The method according to claim 1, wherein a feeding molar ratio of 3-methylthiopropionaldehyde to hydrocyanic acid is 0.95:1 to 0.99:1; a reaction between 3-methylthiopropionaldehyde and the excessive amount of hydrocyanic acid and a reaction between the supplemented 3-methylthiopropionaldehyde and the pre-reaction solution of 2-hydroxy-4-methylthiobutyronitrile have a reaction temperature of 25 to 45° C.

11. The method according to claim 1, wherein said step (2) further comprises a step of conducting an online detection of a residual amount of hydrocyanic acid in 2-hydroxy-4-methylthiobutyronitrile and adjusting the supplementary amount of 3-methylthiopropionaldehyde according to detection results.

12. The method according to claim 1, wherein said step (3) comprises:
subjecting 2-hydroxy-4-methylthiobutyronitrile to hydration reaction in the presence of sulfuric acid in a hydration reactor R5 to form 2-hydroxy-4-methylthiobutyramide, wherein a residual amount of 2-hydroxy-4-methylthiobutyronitrile in reaction solution is detected online and an amount of sulfuric acid to be used is adjusted according to detection results, so as to enable a complete hydration reaction; and
mixing 2-hydroxy-4-methylthiobutyramide with water and then allowing the mixture to enter a hydrolysis reactor R6, so as to prepare 2-hydroxy-4-methylthiobutyric acid via hydrolysis reaction.

13. The method according to claim 12, wherein the hydration reactor R5 and/or the hydrolysis reactor R6 is a multi-stage stirred reactor with a number of stirring stages of 3 to 20.

14. The method according to claim 12, wherein said step (3) further comprises the following steps: adjusting the pH value of 2-hydroxy-4-methylthiobutyric acid to 1 to 2, so as to obtain a neutralized solution of 2-hydroxy-4-methylthiobutyric acid; allowing the neutralized solution of 2-hydroxy-4-methylthiobutyric acid to enter an extraction tower for extraction; and allowing an extract liquor containing 2-hydroxy-4-methylthiobutyric acid to enter a stripping tower, so as to obtain 2-hydroxy-4-methylthiobutyric acid from the bottom of the stripping tower; an extraction solvent of the neutralized solution of 2-hydroxy-4-methylthiobutyric acid is one selected from methyl isobutyl ketone, butanone, pentanone, hexanone and methyl tert-butyl ether; and a mass ratio of the extraction solvent to the neutralized solution of 2-hydroxy-4-methylthiobutyric acid is 0.3:1 to 3:1.

15. The method according to claim 14, wherein the extraction tower is a multi-stage stirred extraction tower with a number of stirring stages of 10 to 30; the stripping tower is a plate tower with a number of plates of 10 to 40.

16. The method according to claim 1, wherein an online Raman spectroscopic detection is employed in the online detection.

* * * * *